(12) United States Patent
Yang et al.

(10) Patent No.: US 8,499,612 B2
(45) Date of Patent: Aug. 6, 2013

(54) HYDROGEN GAS DETECTION USING SINGLE PALLADIUM NANOWIRES

(75) Inventors: Fan Yang, Irvine, CA (US); Reginald M. Penner, Newport Beach, CA (US)

(73) Assignee: The Regents of the University of California, Oakland, CA (US)

( * ) Notice: Subject to any disclaimer, the term of this patent is extended or adjusted under 35 U.S.C. 154(b) by 131 days.

(21) Appl. No.: 12/766,743

(22) Filed: Apr. 23, 2010

(65) Prior Publication Data

US 2010/0269569 A1 Oct. 28, 2010

Related U.S. Application Data

(60) Provisional application No. 61/172,125, filed on Apr. 23, 2009.

(51) Int. Cl.
*G01N 7/00* (2006.01)
(52) U.S. Cl.
USPC .......................... 73/23.2; 73/31.06; 977/957
(58) Field of Classification Search
USPC ...................... 73/23.2, 31.06; 977/748, 957
See application file for complete search history.

(56) References Cited

U.S. PATENT DOCUMENTS

2003/0079999 A1* 5/2003 Penner et al. ................. 205/775
2005/0155858 A1* 7/2005 Monty et al. ................. 204/424

OTHER PUBLICATIONS

Lewis, FA, *The Palladium-Hydrogen System*; Academic Press, London—New York (1967); Chapter 3, pp. 43-49, and Chapter 4, pp. 50-62.

Flanagan, T. B.; Oates, W. A. *The Palladium-Hydrogen System*; Annual Reviews, Inc.: Palo Alto, CA, 1991; vol. 21, pp. 269-304.
Hughes, R. C.; Schubert, W. K. *Journal of Applied Physics* 1992, 71, 542-544.
Favier, F.; Walter, E.; Zach, M.; Benter, T.; Penner, R. *Science* 2001, 293, 2227-2231.
Favier Walter, E.; F.; Penner, R. *Analytical Chemistry* 2002, 74, 1546-1553.
Dankert, O.; Pundt, A. *Applied Physics Letters* 2002, 81, 1618-1620.
Kaltenpoth, G.; Schnabel, R; Menke, E.; Walter, E.; Grunze, M.; Penner, R. *Analytical Chemistry* 2003, 75,4756-476.
Xu, T.; Zach, M.; Xiao, Z.; Rosenmann, D.; Welp, U.; Kwok, W.; Crabtree, G. *Applied Physics Letters* 2005, 86, 203104.
Luongo, K.; Sine, A.; Bhansali, S. *Sensors and Actuators B-Chemical* 2005, 111, 125-1.
Khanuja, M.; Varandani, D.; Mehta, B. R. *Applied Physics Letters* 2007, 91, 253121.
Ibanez, F. J.; Zamborini, F. P. *Journal of the American Chemical Society* 2008, 130, 622-633.
Im, Y.; Lee, C.; Vasquez, R.; Bangar, M.; Myung, N.; Menke, E.; Penner, R.; Yun, M. *Small* 2006, 2, 356-358.
Kiefer, T.; Favier, F.; Vazquez-Mena, O.; Villanueva, G.; Brugger, J. *Nanotechnology* 2008, 19, 125502.
Kim, K.; Sim, S.; Cho, S. *Ieee Sensors Journal* 2006, 6, 509-513.

(Continued)

*Primary Examiner* — Lisa Caputo
*Assistant Examiner* — Punam Roy
(74) *Attorney, Agent, or Firm* — Kenneth S. Roberts; ONE LLP

(57) ABSTRACT

Devices and methods for fast, sensitive hydrogen gas detection using a single palladium nanowire. In one embodiment, a hydrogen sensor comprises a palladium nanowire extending between metal contacts. The palladium nanowire is not subject to fracturing when exposed to hydrogen. The nanowire is able to rapidly and reversibly detect hydrogen as a resistance increase down to 2 ppm with excellent reproducibility and baseline stability at room temperature.

8 Claims, 5 Drawing Sheets

(56) References Cited

OTHER PUBLICATIONS

Mubeen, S.; Zhang, T.; Yoo, B.; Deshusses, M. A.; Myung, N. V. *Journal of Physical Chemistry C* 2007, 111, 6321-632.
Menke, E. J.; Thompson, M. A.; Xiang, C.; Yang, L. C.; Penner, R. M. *Nat Mat* 2006, 5, 914-919.
Xiang, C.; Kung, S. C.; Taggart, D.; Yang, F.; Thompson, M. A.; Mel!, A. G.; Yang, Y.; Penner, R. M. *ACS Nano* 2008, 2, 1939-1949.
Petch, N. *J. Iron and Steel Institute* 1953, 25-28.
Hall, E. *Phys. Soc., Ser. B* 1951, 64, 747-753.
Carlton, C. E.; Ferreira, P. J. *Acta Materialia* 2007, 55, 3749-3756.

\* cited by examiner

HYDROGEN GAS DETECTION USING SINGLE PALLADIUM NANOWIRES

CROSS-REFERENCE TO RELATED APPLICATION

This application claims the benefit of provisional application Ser. No. 61/172,125 filed Apr. 23, 2009, which is fully incorporated herein by reference.

FIELD

The present invention relates generally to palladium based hydrogen sensors and, more particularly, to fast, sensitive hydrogen gas detection using single palladium nanowires.

BACKGROUND

Hydrogen ($H_2$) gas sensors that are sensitive, rapid-responding, stable, compact, and inexpensive are needed to optimize the performance and insure the safety of devices like fuel cells that are powered by $H_2$. Palladium (Pd) nanowires are attractive candidates for $H_2$ sensors because they are able to equilibrate rapidly with $H_2$, leading to a rapid response time. Palladium absorbs hydrogen to form a hydride ($PdH_x$) with x saturating at 0.67 and since 1869 it has been known that the electrical resistivity of this hydride increases linearly with x by a factor of 1.8-1.9 over the range from x=0 to 0.67 (see, Lewis, Academic Press, 1967; Flanagan, Annual Reviews 1991, 21. 269-304). This property of $PdH_x$ was first exploited for hydrogen sensing by Hughes and Schubert (J. Applied Physics 1992, 71, 542-544). As hydrogen gas sensors, Pd resistors are elegant in their simplicity but they have several deficiencies: 1) Hydrogen atom diffusion in palladium is slow at room temperature ($D_H=3.8\times10^{-7}$ $cm^2/s$ at 298K). This means that the Pd resistor must be heated to 70° C. or higher to activate diffusion degrading the power efficiency of the device, 2) The alpha to beta phase transition of $PdH_x$, occurring over the range from 1-2% $H_2$, mechanically stresses the resistor causing deformation and delamination while simultaneously retarding the sensor response time, 3) hydrogen sulfide, ammonia, water, and hydrocarbons interfere with $H_2$ detection at Pd because they dissociatively chemisorb to produce adsorbed hydrogen atoms.

By reducing the distance over which hydrogen must diffuse within the palladium sensing element, the retarding effect of slow proton diffusion on the response time of the resistor is minimized. Early sensors consisted of ensembles of hundreds of Pd nanowires, 150-300 nm in diameter. Exposure of these nanowires to $H_2$ at concentrations above 2% caused each nanowire to fracture approximately every 2 μm along its axis resulting in a loss of electrical continuity (see, Favier, Science, 2001, 293, 2227-2231). Subsequent exposures to $H_2$ above 1-2% threshold for the alpha to beta phase transition swelled the nanowire and closed these fractures, restoring electrical continuity. These sensors had a rapid response time of less than one second, but the limit-of-detection ($LOD_{H_2}$) was in the 2% range necessary to induce the alpha to beta phase transition. This $LOD_{H_2}$ is too high even for $H_2$ leak detection since the lower explosion limit for $H_2$ of 4% is just incrementally higher.

Since 2002, palladium nanostructures have been used in a variety of innovative ways as resistor-based hydrogen sensors. These sensors can be categorized according to the mechanism by which they transduce hydrogen: Sensors that derive their signal from the volume change associated with the alpha to beta phase transition generally show decreased resistance in the presence of hydrogen (i.e., $\Delta R_{H_2}(-)$) while those that measure the increased resistance of the $PdH_x$ relative to Pd show an increased resistance upon $H_2$ exposure (i.e., $\Delta R_{H_2}(+)$). Two dimensional palladium nanoparticulate films fall into the first category. An attribute of these systems is that they often have rapid response times (<1 s) that mimic the early palladium nanowire arrays, but they are much easier to fabricate. Single electrodeposited palladium nanowires have been shown to function as $H_2$ sensors in this $\Delta R_{H_2}(-)$ mode (see, Yun, Small 2006, 2, 356-358). A $\Delta R_{H_2}(-)$ sensors have also produced by using a focused ion beam to cut a nanotrench with width 100-400 nm into a palladium microwire (see, Kiefer, J. Nanotechnology, 2008, 19, 25502). With a few exceptions, $\Delta R_{H_2}(-)$ sensors show a $LOD_{H_2}$ in the 1-2% range coinciding with the threshold for the alpha to beta phase transition. A lower $LOD_{H_2}$ can be obtained for systems capable of functioning in the $\Delta R_{H_2}(+)$ regime because the increased resistance of $PdH_x$ can be detected well below the 1-2% threshold for the alpha to beta phase transition, often at the expense of slower sensor response and recovery times. Recently, a sensitive $\Delta R_{H_2}(+)$ hydrogen sensor was obtained when carbon nanotubes arrayed between two electrical contacts were electrochemically decorated with palladium nanoparticles. These sensors showed a $LOD_{H_2}$ of 100 ppm with response times in the 5-10 minute range (see, Myuang, J. Phys. Chem. 2007, 111, 6321-6327).

Therefore, it is desirable to have palladium nanowire hydrogen sensor with a $LOD_{H_2}$ below 1-2% and an fast response time.

SUMMARY

The embodiments provided herein are generally directed to devices and methods for fast, sensitive hydrogen gas detection using a single palladium nanowire. For nanowires of pure palladium, a subtle difference in grain structure is associated with disparate wire behavior upon exposure to hydrogen gas leading to radically altered functionality in the application of these nanowires as hydrogen sensors. Specifically, single nanowires prepared from EDTA (ethylenediaminetetraacetic acid) containing plating solution are not subject to fracturing when exposed to hydrogen and, for this reason, they are able to rapidly and reversibly detect hydrogen as a resistance increase down to 2 ppm with excellent reproducibility and baseline stability at room temperature.

In one embodiment, a hydrogen sensor comprises a palladium nanowire extending between metal contacts. The palladium nanowire is not subject to fracturing when exposed to hydrogen.

Other systems, methods, features and advantages of the invention will be or will become apparent to one with skill in the art upon examination of the following figures and detailed description.

BRIEF DESCRIPTION OF THE DRAWINGS

The details of the invention, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DESCRIPTION

Figure 1:
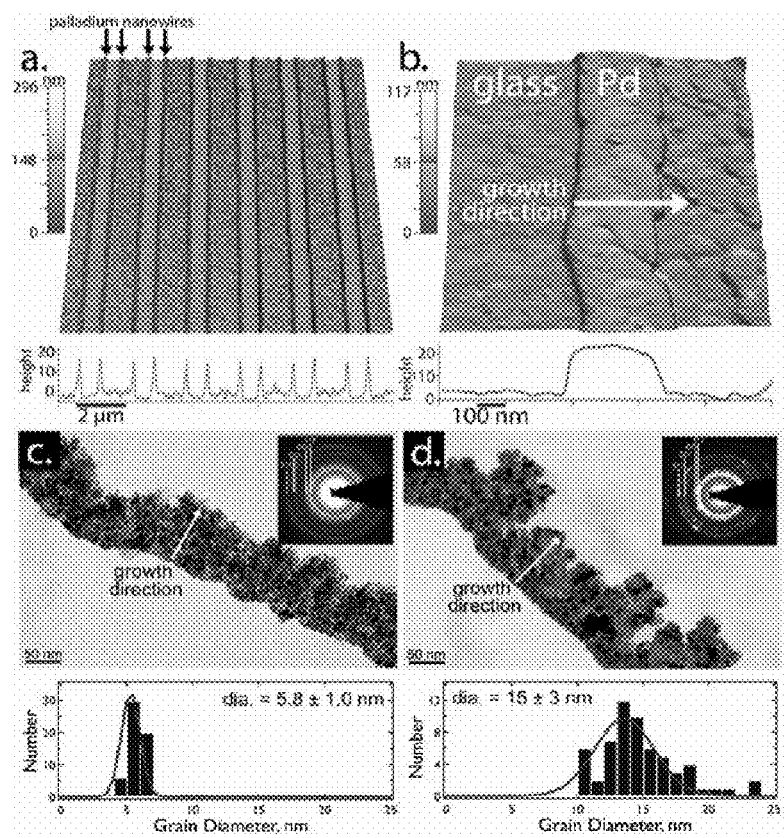
FIGS. 1a-1d are atomic force microscope images of Pd nanowires at low (a) and high (b) magnification, and transmission electron microscope images (c, d) of Pd nanowires prepared in the absence of EDTA (c) and in the presence of EDTA (d) showing the grain structure. Grain diameter histograms for wires of each type are also shown.

The various embodiments and examples provided herein are generally directed to devices and methods for fast, sensitive hydrogen gas detection using a single palladium nanowire. For nanowires of pure palladium, a subtle difference in grain structure is associated with disparate wire behavior upon exposure to hydrogen gas leading to radically altered functionality in the application of these nanowires as hydrogen sensors. Specifically, as described below, single nanowires prepared from EDTA (ethylenediaminetetraacetic acid) containing plating solution are not subject to fracturing when exposed to hydrogen and, for this reason, they are able to rapidly and reversibly detect hydrogen as a resistance increase down to 2 ppm with excellent reproducibility and baseline stability at room temperature. By controlling the grain structure of a palladium nanowire, a palladium nanowire operating in either the $RH_2$(+) or the $RH_2$ (−) modes can be obtained. As described below, superior $H_2$ sensing performance, including response times in the 1-5 s range upon exposure to high $H_2$ concentrations and a $LOD_{H_2}$ of 2 ppm have been demonstrated for single Pd nanowire sensors operating in the _$RH_2$ (+) mode upon exposure to $H_2$.

As described below, two types of pure palladium (Pd) nanowires, differentiated by microstructure, were electrodeposited: 1) nanocrystalline Pd nanowires with a grain diameter of 5 nm (henceforth nc5-Pd), and, 2) nanocrystalline Pd nanowires with a grain diameter of 15 nm (nc15-Pd). These nanowires were evaluated for the detection of hydrogen gas ($H_2$). In spite of their fundamental similarities, the behavior of these nanowires upon exposure to $H_2$ was dramatically and reproducibly different. For instance, the nc5-Pd nanowires spontaneously fractured upon exposure to $H_2$ above 1-2%. The fractured nanowires continued to function as sensors for $H_2$ concentrations above 2%, actuated by the volume change associated with the alpha to beta phase transition of PdHx. In contrast, the nc15-Pd nanowires, in contrast, withstood repeated exposures to $H_2$ up to 10% without fracturing. nc15-Pd nanowires showed a rapid (2 s at 8%) increase in resistance in the presence of $H_2$, and a response that scaled smoothly with $H_2$ concentration spanning five orders of magnitude down to 2 ppm.

The Pd nanowires described herein were prepared using lithographically patterned nanowire electrodeposition (LPNE) (see, Menke, Nt. Mat. 2006, 5, 914-919; Xiang, ACS Nano 2008, 2, 1939-1949 (which are incorporated herein by reference)). The nc5-Pd nanowires were prepared by electrodepositing Pd on a substrate at a potential of +0.18 V vs. saturated calomel electrode (SCE) from an aqueous electrolyte (0.2 mM PdCl2, 0.1 M KCl, pH=4.9) at current densities approximately one order of magnitude below diffusion control. The nc15-Pd nanowires were electrodeposited at a potential of −0.80 V vs. SCE from the same aqueous electrolyte except for the addition of about 0.22 mM ($10^{-3}$ Mole) of EDTA (ethylenediaminetetraacetic acid). The complexation of palladium ion by EDTA caused a negative shift in the threshold for Pd deposition, but the deposition potential more than compensated for this shift, producing a deposition rate that was an order of magnitude larger than that used in the EDTA-free Pd depositions. The goal is to complex all of the palladium, the addition of EDTA to the electrolyte is preferably in the range of about 0.05 to 10.0 mM.

LPNE produces nanowires that have a rectangular cross-section with a well-defined height and width that are independently adjustable over a wide range. As described herein, nanowires ranging in height from 11 nm to 48 nm and in width from 36 nm to 93 nm. An array of palladium nanowires produced by LPNE are shown in the atomic force microscope (AFM) images of FIG. 1a and FIG. 1b. The AFM images of nanowires deposited from EDTA-free and EDTA-containing solutions were identical, but, as depicted in FIGS. 1c and 1d, important morphological differences between them are readily apparent in transmission electron micrographs which were acquired at 9 tilt angles (−8° to +8° at 2° increments) in order to facilitate the identification of individual grains. In these bright-field images, individual Pd grains become dark when their crystallographic orientation meets the condition for diffracting the electron beam, deflecting it off the detector. The grain size distribution is obtained by measuring these darkened grains in a series of tilted images. Just one TEM image from each series is shown in FIGS. 1c and 1d, together with the grain diameter histograms assembled from these two tilt series. These images show that Pd nanowires deposited from the EDTA-free solution, i.e., the nc5-Pd nanowires, are nanocrystalline with a narrow grain diameter distribution peaking at 5.8 nm. In the micrograph of FIG. 1c, the 5-6 nm grains are all approximately round and the wire morphology is quite open, with cracks and voids apparent between grains, especially at wire edges. Wires deposited in the EDTA-containing electrolyte, i.e., the nc15-Pd nanowires, had a larger mean grain diameter of 15 nm and a broader distribution of grain diameters. The nc15-Pd nanowires also have a more compact, electron dense morphology in spite of the fact that both nanowires shown here had the same total thickness of 20 nm. It is possible that carbon incorporation occurs for the nc15-Pd nanowires deposited from the EDTA-containing solution, but carbon was not detected above background in EDAX (x-ray fluorescence) elemental analyses of these nanowires. Thus, both the nc5-Pd and nc15-Pd nanowires are nanocrystalline, but as discussed below, the subtle morphological differences seen in FIGS. 1c and 1d translate into dramatic differences in their hydrogen sensing performance.

Figure 2:
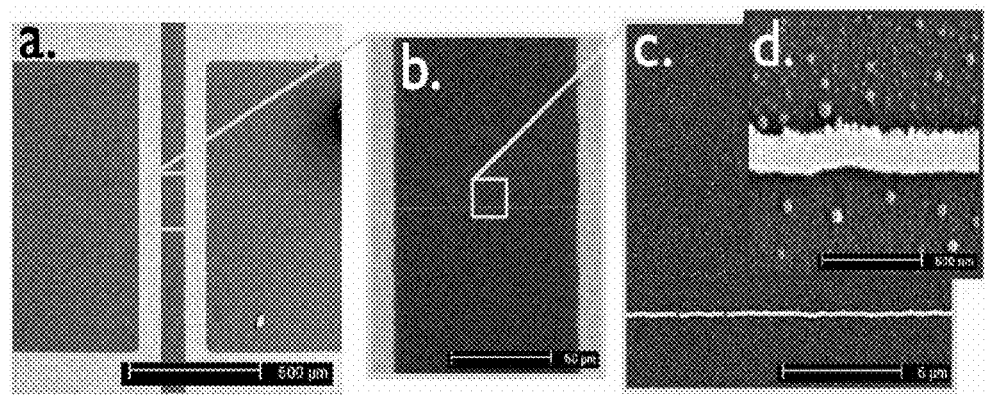
FIG. 2a-2c are scanning electron microscope images at progressively higher magnification of a Pd nanowire-based $H_2$ sensor consisting of a single Pd nanowire with evaporated contact electrodes.

As depicted in FIG. 2a, hydrogen sensors were fabricated from single Pd nanowires supported on glass by evaporating gold electrical contacts (FIG. 2a) and attaching copper wires to these contacts using silver paint. As depicted in FIG. 2b, these evaporated contacts isolated a 100 μm length of each nanowire. The electrical resistance of this wire section was measured using four electrical contacts as a function of time during the exposure of the sensor to pulses of hydrogen of predetermined concentration in a flowing stream of pure nitrogen gas.

A plot of resistance versus time for the exposure of a single nc5-Pd nanowire to a series of hydrogen pulses near 1% is shown in FIG. 3a. An increase in the wire resistance ($\Delta R/R_o \approx 15\%$) is seen during each hydrogen exposure for the first five of these pulses and then, during the sixth pulse, the resistance increases to more than 10 MΩ. This rapid increase in resistance signals the formation of fractures in the Pd nanowire. After fracturing, the nc5-Pd nanowire shows no detectable response to $H_2$ exposure below 1%, but for higher concentrations, the nanowire resistance rapidly and reversibly decreases and the amplitude of this resistance change, plotted as an increased conductance in FIG. 3c, correlates with the $H_2$ over a narrow concentration range of 1-5%. For $H_2$ above 5%, no change in conductance is seen over that measured at 5%. Over range of 1-5%, the reproducibility of the conductance change is 10-20% as shown in FIG. 3b. These response characteristics are, in all respects, similar to those reported for other $\Delta R_{H_2}(-)$ sensors that transduce H2 using the alpha to beta phase transition of $PdH_x$.

Figure 3:
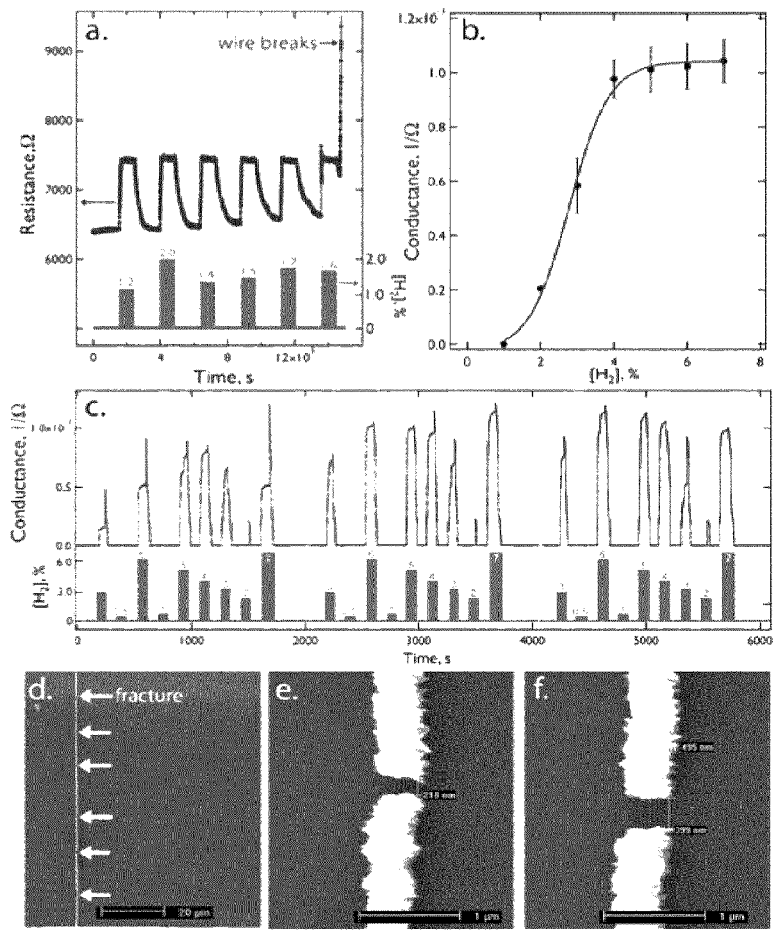
FIG. 3a includes plots of resistance versus time during the exposure of a single 40×430 nm Pd nanowire to pulses of 1.2%-1.6% hydrogen. Fracture of the nanowire on the sixth exposure is signaled by an increase in the resistance to >1 M$\Omega$.
FIG. 3b is a calibration plot for the response of a fractured nc5-Pd nanowire to $H_2$. Error bars indicate±one standard deviation of the mean for multiple trials.
FIG. 3c is a plot of conductance versus time for the exposure of a fractured nc5-Pd nanowire to pulses of hydrogen ranging in concentration from 0.5% to 7%.
FIGS. 3d-3f are scanning electron microscope images at low magnification (d) and higher magnification (e,f) showing fractures produced by $H_2$ exposure.

The occurrence of fracturing of the nc5-Pd nanowires was confirmed by SEM examination of the nc5-Pd nanowire after exposure to H2 as shown in FIG. 3d. These nanowires are fractured periodically, every 10 μm along the nanowire length with each fracture defined by a 200-400 nm gap. The integrated gap length along each fractured nanowire corresponds to 3-4%, approaching the expected 3.5% linear expansion induced by the alpha to beta phase transition of $PdH_x$. In previous studies, the properties of ensembles of 200 nm diameter Pd nanowires for sensing hydrogen, the same fracturing behavior was observed in response to hydrogen exposure for these much larger nanowires. In 13 trials involving the exposure of the nc5-Pd nanowires to hydrogen in the concentration range near 1%, all 13 nanowire fractured in the manner depicted in FIG. 3. Thus, it is apparent that the sensing mechanism for fractured nc5-Pd nanowires involves the mechanical closing of these fractures upon exposure to H2 above 1% caused by the alpha to beta phase transition of $PdH_x$ and the simultaneous swelling by 2.5% of the $PdH_x$ wire's linear dimensions relative to Pd. A suspended wire in tension should fracture once, not multiple times, so the existence of multiple fractures requires multiple strong points of attachment between the wire and the glass surface—a minimum of one per fracture—arrayed along each nanowire.

Figure 4:
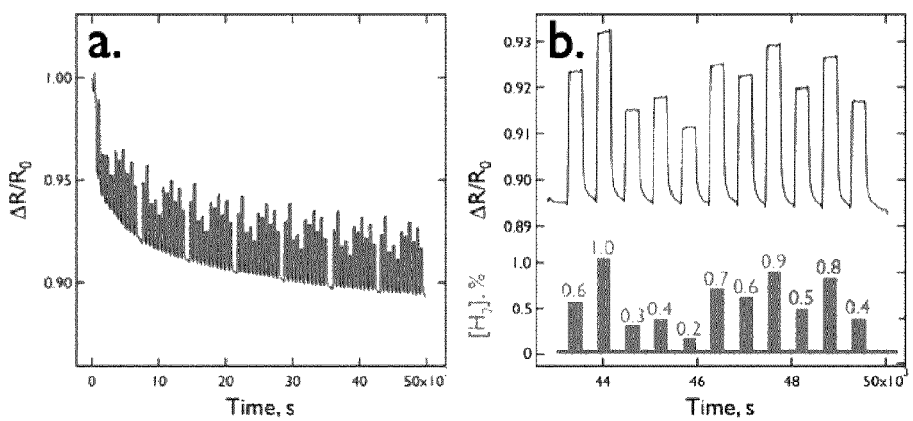
FIG. 4a-4b are plots of (a) $\Delta R/R_0$ versus time for the exposure to 77 pulses of $H_2$ ranging in concentration from 0.2% to 1.0% and (b) $\Delta R/R_0$ versus time for the final sequence of eleven $H_2$ exposures comparing the applied concentration program (bottom) with the observed nanowire response (top) for the initial exposures of a 20×42 nm nc15-Pd nanowire to $H_2$.

Individual nc15-Pd nanowires produced from EDTA containing electrolyte, as described above, did not fracture upon exposure to hydrogen at any concentration. As a result, these nanowires to operate in the $\Delta R_{H_2}(+)$ mode, enabling far superior H2 sensing performance as compared with nc5-Pd nanowires. The resistance of a freshly prepared nc15-Pd nanowire is shown in FIG. 4a as it is repeatedly exposed to a sequence of $H_2$ pulses ranging in concentration from 0.2 to 1.0% over 14 hours. Significant drift of the baseline resistance is seen in this data but the drift decreases progressively over the 14 hour experiment until at its conclusion, it is reduced to $\Delta R/R_0 \approx 0.09\%$/hour. Each nc15-Pd nanowire employed for sensing was preconditioned to stabilize its baseline resistance using this procedure.

Figure 5:
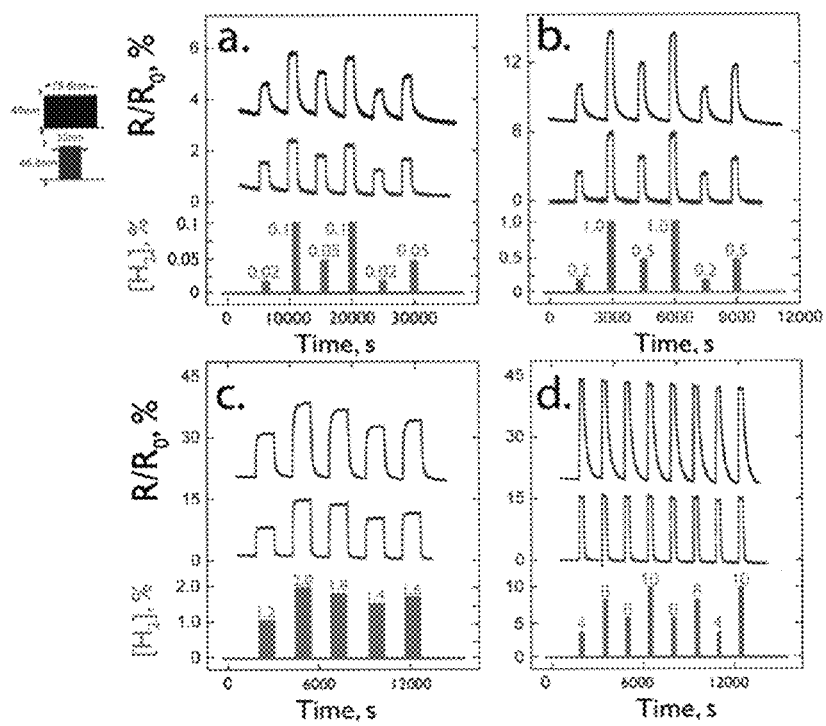
FIG. 5a-5d are plots of (a) 0.02% to 0.1% pulses with a duration of 9 hour, (b) 0.2% to 1.0% $H_2$ pulses with a duration of 3 hour, (c) 1.2% to 2.0% $H_2$ pulses with a duration of 3.5 hour, and (d) 4% to 10% $H_2$ with a duration of 3.5 hour for a $\Delta R/R_0$ response of two nc15-Pd nanowire sensors (inset) over a wide $H_2$ concentration range.
Figure 6:
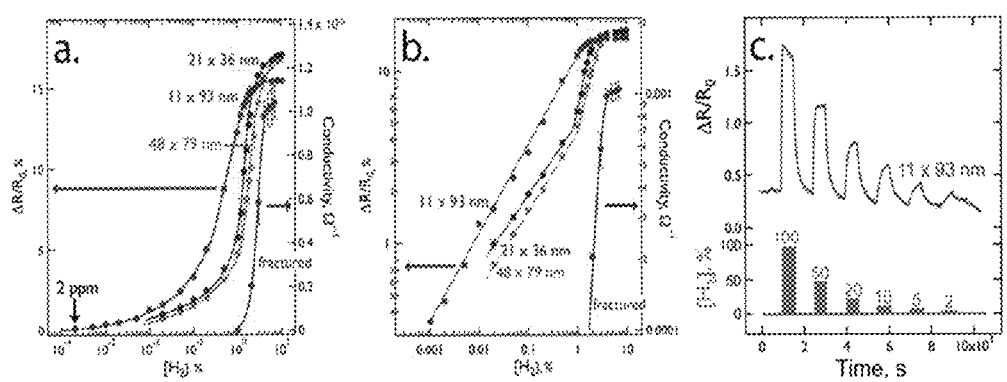
FIG. 6a-6c are calibration curves for three nc15-Pd nanowires and a fractured nc5-Pd nanowire including (a) $\Delta R/R_0$ (or conductivity) versus Log $H_2$ concentration response, (b) Log-Log representation of the same data shown in (a), and (c) response of the 11×93 nm nc15-Pd nanowire to $H_2$ concentration from 2 to 100 ppm.

As shown in FIG. 5, raw sensing data for two different nc15-Pd nanowires shows rapid, reversible increases in resistance for $H_2$ ranging from 0.02% to 10%. But the signal-to-noise seen in FIG. 5a at the lower end of this range supports the detection of much lower $H_2$, down to 2 ppm (see FIG. 6c). Referring to FIGS. 6a and b, calibration plots for nanowires of different widths and heights show very clearly the extended concentration range over which the nc15-Pd nanowires are able to operate relative to the nc5-Pd nanowires (labeled "fractured"). Less obvious, but of equal importance, is a tremendous improvement in the reproducibility of the $\Delta R/R_0$ seen at each concentration which is reflected by the error bars in each data set. These calibration plots also reveal that $\Delta R/R_0$ is insensitive to the lateral wire dimensions, and its initial resistance, to first order. For example, the electrical resistance of the smaller nanowire (21×36 nm) was 305 KΩ and that of the larger nanowire (48×79 nm) was 40.8 KΩ, but these two nanowires produced the same $\Delta R/R_0$, to within 5% over the entire concentration range from $H_2$=0.02 to 10%.

Figure 7:
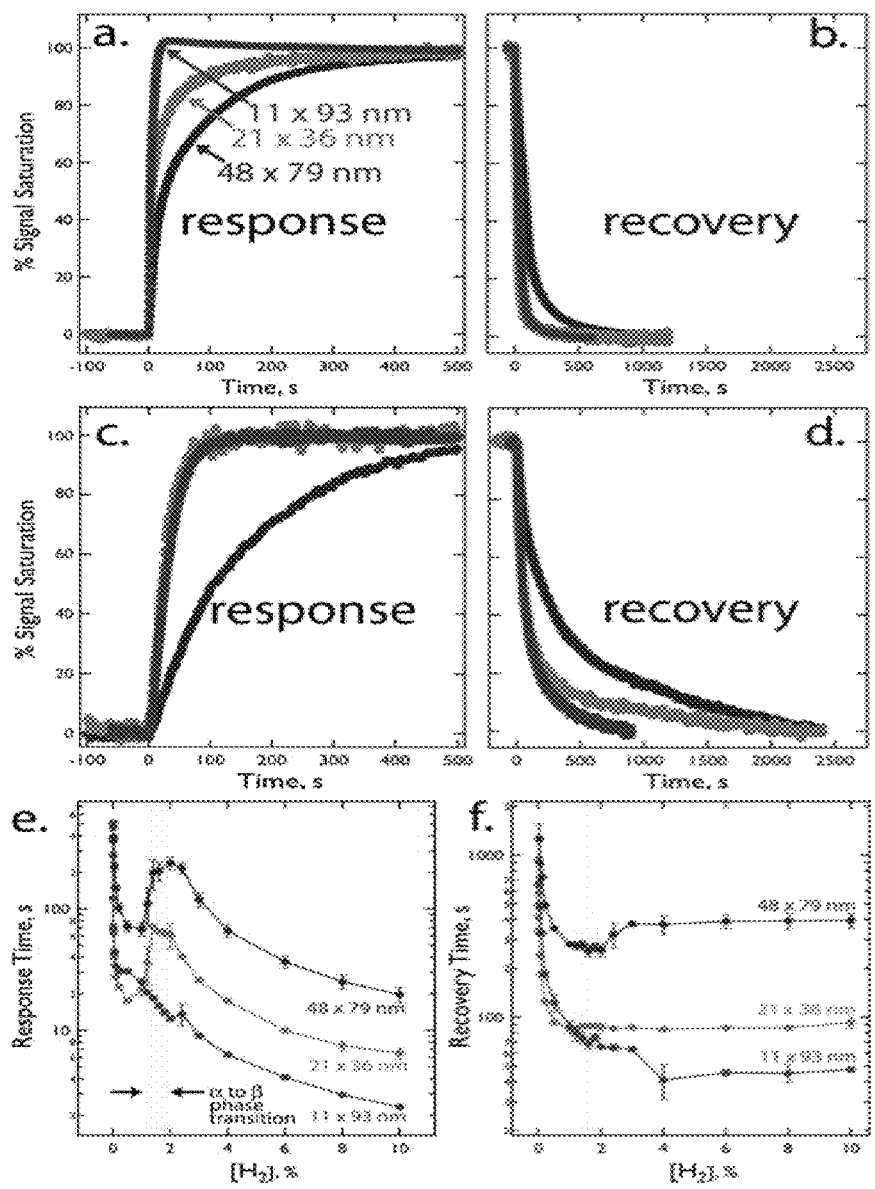
FIG. 7a-7f are graphs providing a comparison of temporal response characteristics for three nc15-Pd nanowires including (a) response to $H_2$=10%, (b) recovery from exposure to $H_2$=10%, (c) response to $H_2$=0.02%, (d) recovery from exposure to $H_2$=0.02%, (e) summary of response times as a function of $H_2$ concentration for three nc15-Pd nanowires, and (f) summary of recovery times as a function of $H_2$ concentration for the same three nanowires.

However, as shown in FIG. 7, the response and recovery times for nc15-Pd nanowires, on the other hand, were strongly dependent on the wire lateral dimensions. These two metrics are defined as the time necessary for the $\Delta R/R_0$ to achieve 90% of their respective values at infinite time. Two features of the data shown in FIG. 7 are worth noting: First, above $H_2$ concentration of 1%, response and recovery times decrease by approximately an order of magnitude as the wire height is reduced from 48 nm to 21 nm to 11 nm in spite of the fact that the wire width does not change monotonically for these three wires. Thus, the wire height is the main predictor of the temporal response and recovery times for nc15-Pd nanowires. For lower $H_2$ concentration, the effect of wire size is still present but somewhat weaker. Second, the response time for the nanowires with a height of 21 nm and 48 nm is retarded by the alpha to beta phase transition leading to a peak in the response time versus $H_2$ concentration of FIG. 7e at 1-2%. The existence of this peak tells us that the alpha to beta phase transition prevents nanowires from rapidly equilibrating with the hydrogen concentration, particularly at the $H_2$ concentration of 1-2% threshold for the phase transition. This slowing of the sensor response depends strongly on the lateral dimensions of the nanowires and it is not observed at all for the smallest nanowire examined, with (h)=11 nm. The implication is that smaller nanowires are able to more rapidly accommodate the strain imposed by the ≈10% volume change associated with this phase transition.

Figure 8:
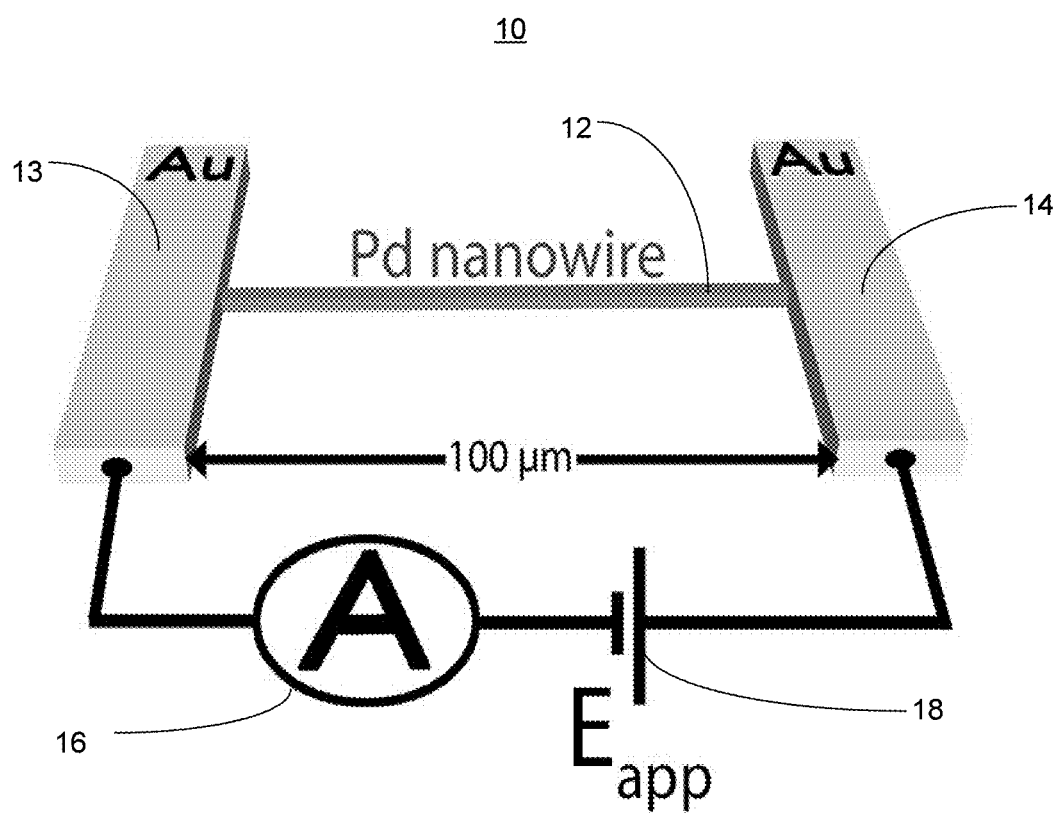
FIG. 8 is a schematic of a palladium nanowire based hydrogen sensor.

Turning to FIG. 8, a palladium nanowire based hydrogen sensor 10 is shown. As depicted, the sensor 10 preferably comprises a palladium nanowire 12 extending between first and second contacts 13 and 14 preferably form of gold or other metal. A power source 18 and an amp meter 16 to measure the resistance of the nanowire 12 upon exposure to hydrogen are coupled to the first and second contacts 13 and 14. The nanowire 12 is preferably not subject to fracture upon exposure to hydrogen and is preferably form from an EDTA containing plating solution. As depicted, the nanowire 10 includes a square or rectangular cross-sectional shape and is about 100 µm in length.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

The invention claimed is:

1. A hydrogen sensor comprising
first and second electrical contacts, and
a palladium nanowire coupled to and extending between the first and second electrical contacts, wherein the nanowire is electrically continuous along its length and exposable to hydrogen for concentrations up to about 10% without fracturing to cause gaps along its length in the absence of hydrogen.

2. A hydrogen sensor comprising
first and second electrical contacts, and
a palladium nanowire extending between the first and second electrical contacts, wherein the nanowire is electrically continuous along its length and exposable to hydrogen for concentrations up to about 10% without fracturing to cause gaps along its length in the absence of hydrogen, wherein an increase in resistance of the nanowire is detectable in the presence of hydrogen for concentrations down to 2 ppm.

3. The hydrogen sensor of claim 2 wherein the increase in resistance of the nanowire is detectable in the presence of hydrogen in a range of 1 to 5 seconds.

4. A hydrogen sensor comprising
first and second electrical contacts, and
a palladium nanowire extending between the first and second electrical contacts, wherein the nanowire is electrically continuous along its length and exposable to hydrogen for concentrations up to about 10% without fracturing to cause gaps along its length in the absence of hydrogen, wherein an increase in resistance of the nanowire is detectable in the presence of hydrogen in a range of 1 to 5 seconds and wherein the increase in resistance of the nanowire is detectable in the presence of hydrogen in a range of 1-2% hydrogen.

5. The hydrogen sensor of claim 1 further comprising a power source coupled to the first and second contacts.

6. The hydrogen sensor of claim 5 further comprising a means for measuring an increase in resistance of the nanowire coupled to the first and second contacts.

7. The hydrogen sensor of claim 5 further comprising an amp meter for measuring an increase in resistance of the nanowire coupled to the first and second contacts.

8. The hydrogen sensor of claim 1 wherein an increase in resistance of the nanowire is detectable in the presence of hydrogen in a range of 1 to 5 seconds.

* * * * *